(12) United States Patent
Shin et al.

(10) Patent No.: US 11,234,919 B2
(45) Date of Patent: Feb. 1, 2022

(54) COMPOUND PRODUCED BY MEANS OF MARINE MICROORGANISM AND COMPOSITION FOR IMPROVING SKIN WRINKLES, ENHANCING ELASTICITY AND SKIN WHITENING COMPRISING SAME COMPOUND AS ACTIVE INGREDIENT

(71) Applicant: KOREA INSTITUTE OF OCEAN SCIENCE & TECHNOLOGY, Busan (KR)

(72) Inventors: Heejae Shin, Suwon-si (KR); Gambang Pil, Seoul (KR); Hyiseung Lee, Seoul (KR); Jongseok Lee, Ansan-si (KR); Yeonju Lee, Gunpo-si (KR); Jihoon Lee, Anyang-si (KR)

(73) Assignee: Korean Institute of Ocean Science & Technology, Busan (KR)

( * ) Notice: Subject to any disclaimer, the term of this patent is extended or adjusted under 35 U.S.C. 154(b) by 173 days.

(21) Appl. No.: 16/634,046

(22) PCT Filed: Sep. 26, 2017

(86) PCT No.: PCT/KR2017/010572
§ 371 (c)(1),
(2) Date: Jan. 24, 2020

(87) PCT Pub. No.: WO2019/022294
PCT Pub. Date: Jan. 31, 2019

(65) Prior Publication Data
US 2021/0145721 A1 May 20, 2021

(30) Foreign Application Priority Data
Jul. 25, 2017 (KR) ........................ 10-2017-0093952

(51) Int. Cl.
| | |
|---|---|
| *A61K 8/49* | (2006.01) |
| *A23L 33/10* | (2016.01) |
| *A23L 33/00* | (2016.01) |
| *A61Q 19/02* | (2006.01) |
| *A61Q 19/08* | (2006.01) |
| *C07D 309/36* | (2006.01) |
| *A61K 31/351* | (2006.01) |
| *C07D 309/38* | (2006.01) |

(52) U.S. Cl.
CPC .............. *A61K 8/498* (2013.01); *A23L 33/10* (2016.08); *A23L 33/40* (2016.08); *A61Q 19/02* (2013.01); *A61Q 19/08* (2013.01); *C07D 309/36* (2013.01); *A23V 2002/00* (2013.01)

(58) Field of Classification Search
CPC ..... A23L 33/10; A23L 33/40; A23V 2002/00; A23V 2200/318; A61Q 19/02; A61Q 19/08; C07D 309/38; C07D 309/36; A61K 31/351; A61K 8/49; A61K 8/498; A61K 8/4973
See application file for complete search history.

(56) References Cited

U.S. PATENT DOCUMENTS 9,499,508 B2 * 11/2016 Carola ................. A61Q 19/06
10,188,592 B2 * 1/2019 Carola ................. A61P 29/00

FOREIGN PATENT DOCUMENTS

| CN | 102070588 | 5/2011 |
|---|---|---|
| EP | 0417632 | 3/1991 |
| EP | 3674296 | 7/2020 |
| KR | 10-20050081703 | 8/2005 |
| KR | 10-0812922 | 3/2008 |

OTHER PUBLICATIONS

Lee, JS; "Recent Advances in the Synthesis of 2-Pyrones"; Marine Drugs (2015), 13, pp. 1581-1620. Published Mar. 23, 2015.*
Biagetti et al., "Selective Synthesis of 5,6-Disubstituted 3-Methyl-2(2H)-pyranones and 6-Substituted 3-Methyl-2(2H)-pyranones, Including Fusalanipyrone and Gibepyrone A," European Chemical Societies Publishing, dated Feb. 20, 2002, 1063-1076.
Cai et al., "A new a-pyrone from the mangrove endophytic fungus Phomopsis sp. HNY29-2B," Natural Product Research, dated Aug. 2016, 31(2): 124-130.
Ciavatta et al., "Aplysiopsenes: an additional example of marine polyketides with a mixed acetate/propionate pathway," Tetrahedron Letters, dated Nov. 2008, 527-529.
Extended European Search Report in European Application No. 17918891.7, dated Nov. 27, 2020, 12 pages.
Geiseler et al., "Total synthesis of infectopyrone, aplysiopsenes A-C, ent-aplysiopsene D, phomapyrones A and D, 8,9-dehydroxylarone, and nectriapyrone," Tetrahedron, dated Jul. 2012, 7280-7287.
Hua et al., Palladium-catalysed anullation of β-chloro-α, β-unsaturated esters with internal alkynes leading to 2H-pyran-2-ones, National Institute of Materials and Chemical Research, dated Dec. 5, 2000, 25:179-184.
Onda et al., "Reinvestigation of the Biomimetic Cydization of 3,5-Diketo Esters: Application to the Total Synthesis of Cyercene A, an a-Methoxy-y-Pyrone-Containing Polypropionate," Synlett, dated Apr. 26, 2017, 28:1596-1600.

(Continued)

Primary Examiner — Jeffrey T. Palenik
(74) Attorney, Agent, or Firm — Fish & Richardson P.C.

(57) ABSTRACT

The present invention relates to a novel compound represented by following formula 2 produced by means of marine-derived fungus Penicillium sp. and a composition for improving skin wrinkles, enhancing elasticity and skin whitening using excellent collagen synthesis promoting activity and melanin production inhibitory activity of the novel compound. In formula 2, $R_1$ is any one selected from the group consisting of H, OH, COOH, an alkyl having 1 to 6 carbon atoms and an alkoxy having 1 to 6 carbon atoms. $R_1$ is any one selected from the group consisting of H, OH, COOH, an alkyl having 1 to 6 carbon atoms and an alkoxy having 1 to 6 carbon atoms. $R_2$ is any one selected from the group consisting of H, OH, COOH, an alkyl having 1 to 6 carbon atoms and an alkoxy having 1 to 6 carbon atoms. $R_3$ is any one selected from the group consisting of H, OH, COOH, an alkyl having 1 to 6 carbon atoms and an alkoxy having 1 to 6 carbon atoms. $R_4$ is any one selected from the group consisting of H, OH, COOH, an alkyl having 1 to 6 carbon atoms and an alkoxy having 1 to 6 carbon atoms.

13 Claims, 5 Drawing Sheets

(56) References Cited

OTHER PUBLICATIONS

Reffstrup et al., "Synthesis of the Antibiotic Monoterpenoid Nectriapyrone," Tetrahedron Letters, dated Apr. 16, 1976, (22): 1903-1904.
Whang et al., "Total Synthesis of (+)-Verrucosidin," Journal of American Chemical Society, dated Nov. 1, 1990, 112(24): 8985-8987.
Xia et al., "Secondary Metabolites Produced by an Endophytic Fungus *Pestalotiopsis sydowiana* and Their 20S Proteasome Inhibitory Activities," Molecules, dated Jul. 20, 2016, 21(7): 944, 8 pages.
Barrero et al., "Gibepyrones: á-pyrones from Gibberella fujikuroi", Tetrahedron, vol. 49 Issue 1, 1993, 10 pages.
Chattapadhyay et al., "Antifungal activity of 4-methyl-6-alkyl-2H-pyran-2-ones", Journal of Agricultural and Food Chemistry, vol. 54 No. 6, 2006, 5 pages.
Fu et al., "á-Pyrones from the marine-derived actinomycete *Nocardiopsis dassonvillei* subsp. *dassonvillei* XG-8-1", RSC Advances, vol. 3 No. 43, 2013, 6 pages.
Paul et al., "New polypropionates from Siphonaria pectinata", Tetrahedron, vol. 53 No. 6, 1997, 6 pages.
PCT International Search Report and Written Opinion in International PCT application No. PCT/KR2017/010572, dated Apr. 23, 2018, 25 pages (With English Translation).

* cited by examiner

¹H and ¹³C NMR data[a] of O20-2

| NO. | $\delta_C$, Type | $\delta_H$, mult. (J in Hz) | COSY | HMBC |
|---|---|---|---|---|
| 1 | | | | |
| 2 | 168.5, qC | | | |
| 3 | 99.2, qC | | | |
| 4 | 170.0, qC | | | |
| 5 | 109.6, qC | | | |
| 6 | 160.2, qC | | | |
| 7 | 9.1, CH₃ | 1.91, s | | 2, 3, 4 |
| 8 | 12.0, CH₃ | 1.97, s | | 4, 5, 6 |
| 1' | 130.1, qC | | | |
| 2' | 132.1, CH | 5.78, q (7) | | 6 |
| 3' | 13.9, CH₃ | 1.80, d (7) | 4' | 1', 2' |
| 4' | 14.7, CH₃ | 1.88, s | | 6, 1', 2' |

[a] ¹H and ¹³C NMR data were measured at 500 and 125 MHz, respectively.

FIG. 6

COMPOUND PRODUCED BY MEANS OF MARINE MICROORGANISM AND COMPOSITION FOR IMPROVING SKIN WRINKLES, ENHANCING ELASTICITY AND SKIN WHITENING COMPRISING SAME COMPOUND AS ACTIVE INGREDIENT

TECHNICAL FIELD

The present disclosure relates to a novel compound produced by marine microorganisms and a composition containing the compound as an active ingredient for skin wrinkle relief, elasticity enhancement, and skin whitening and, specifically, to a novel compound produced by the marine-derived fungus *Penicillium* sp. and a composition for skin wrinkle improvement, elasticity enhancement, and skin whitening by means of the use of excellent collagen synthesis stimulating activity and melanogenesis inhibiting activity of the novel compound.

BACKGROUND ART

Collagen, which is the main matrix protein produced in skin fibroblasts, is present in the extracellular matrix. The important functions of collagen include mechanical firmness of the skin, resistance of connective tissues, connectivity of tissues, support of cell adhesion, induction of cell division and differentiation (upon organism growth or wound healing), and the like. This collagen decreases with age and is reduced by photo-aging due to ultraviolet radiation, and such a reduction of collagen is closely associated with wrinkle formation of the skin. In recent years, the development of extensive research on skin aging has revealed important functions of collagen in the skin.

Cosmetic products mixed with collagen have been conventionally released in consideration of skin moisturizing effects of collagen. However, these cosmetic products result in the application of collagen onto the skin surface, and thus cannot be expected to take a moisturization action by transdermal absorption of collagen, which is a polymer, thereby falling short of substantial skin function enhancement.

There are active ingredients that stimulate collagen synthesis to show a wrinkle relieving effect, and, for example, retinoic acid, transforming growth factor (TGF), animal placenta-derived proteins (Japanese Patent 8-231370), betulinic acid (Japanese Patent 8-208424 Document 2), chlorella extracts (Japanese Patents 9-40523 and 10-36283), and the like are collagen synthesis stimulating substances. However, the active ingredients, when applied to the skin, are limited in the amounts of use due to safety problems, such as irritation and redness, or show an insignificant effect, and therefore, the active ingredients cannot be expected to substantially have a skin function enhancing effect through the simulation of collagen synthesis in the skin. Accordingly, there is an urgent need for the development of an ingredient that is safe for a living body, is stable as an active ingredient, and above all, has more excellent wrinkle relieving activity than existing collagen synthesis simulating substances.

Human skin color is genetically determined by the concentration and distribution of melanin in the skin, and is also affected by environmental or physiological conditions, such as solar ultraviolet radiation, fatigue, and stress. Melanin is produced by converting tyrosine, a kind of amino acid, into DOPA and dopaquinone through a tyrosinase action, followed by non-enzymatic oxidation.

Although the melanogenesis pathway has been known, a mechanism by which melanogenesis is induced before the action of tyrosinase has not yet been revealed in detail.

Therefore, a substance with tyrosinase inhibiting activity, such as hydroquinone, ascorbic acid, kojic acid, or glutathione, has been used in mixture with an ointment or a cosmetic material for the purpose of whitening skin or relieving freckles and melasma. However, the foregoing method caused skin irritation or poor product stability, resulting in an insignificant effect, and thus the method was limited in its use. Accordingly, the development of a novel whitening agent is urgently needed.

DETAILED DESCRIPTION OF THE INVENTION

Technical Problem

An aspect of the present disclosure is to provide a compound capable of being advantageously used for skin wrinkle relief, elasticity enhancement, and skin whitening, and a preparation method for the compound.

Technical Solution

In accordance with an aspect of the present disclosure, there are provided a compound represented by Formula 2 below, and preferably a compound represented by Formula 1 below:

[Formula 2]

wherein, $R_1$ is any one selected from the group consisting of H, OH, COOH, alkyl having 1 to 6 carbon atoms, and alkoxy having 1 to 6 carbon atoms;

$R_2$ is any one selected from the group consisting of H, OH, COOH, alkyl having 1 to 6 carbon atoms, and alkoxy having 1 to 6 carbon atoms;

$R_3$ is any one selected from the group consisting of H, OH, COOH, alkyl having 1 to 6 carbon atoms, and alkoxy having 1 to 6 carbon atoms; and $R_4$ is any one selected from the group consisting of H, OH, COOH, alkyl having 1 to 6 carbon atoms, and alkoxy having 1 to 6 carbon atoms.

[Formula 1]

The compound represented by Formula 1 may be prepared by a microorganism deposited as Accession Number KCTC 13190BP.

In accordance with another aspect of the present disclosure, there are provided a pharmaceutical composition, an externally-applied dermal preparation composition, a cosmetic composition, and a health food composition, each of which contains the compound represented by Formula 1 or 2 and is used for skin wrinkle relief, elasticity enhancement, and skin whitening.

Each of the compositions according to the present disclosure may contain the compound represented by Formula 1 or 2 in 0.0001-10 wt % relative to the entire composition.

Advantageous Effects

The above-described compounds according to the present disclosure show a skin elasticity enhancing effect and a wrinkle relieving effect by stimulating collagen synthesis of skin fibroblasts, show a skin whitening effect through a very excellent melanogenesis inhibiting effect, and can be used for a medicinal product, a cosmetic material, or a health food without side effects due to the absences of cytotoxicity.

MODE FOR CARRYING OUT THE INVENTION

Hereinafter, detailed description for implementing the present disclosure will be made.

The isolation, identification, and culture of the marine fungus *Penicillium* sp. 108YD020 will be first described.

Figure 1:
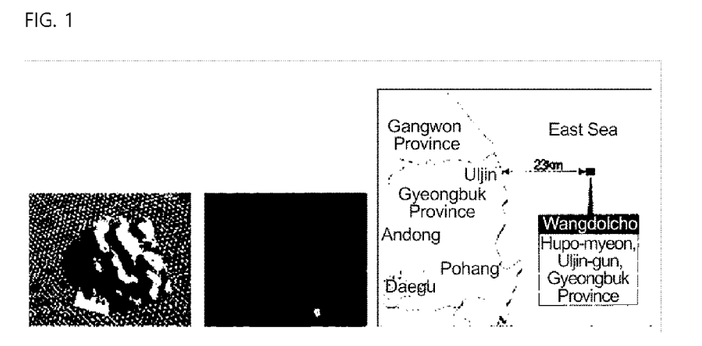
FIG. 1 schematically shows a region where the strain 108YD020 was isolated.

The strain 108YD020 strain was isolated from a sponge (108YD-1) collected at Wangdolcho, East Sea, Korea (see FIG. 1) in August 2010. Approximately 1 g of the collected sponge was placed in a falcon tube filled with 9 ml of sterile seawater, sonicated for 5 min, and then diluted to $10^{-1}$, $10^{-2}$, $10^{-3}$, and $10^{-4}$ by addition of sterile seawater. Three equal portions of 100 μl of the sponge diluted solution were inoculated and uniformly plated using a micropipette on the AIA, HV agar, and BN agar, respectively, and then incubated in the B.O.D incubator at 28° C. for 14 days. The strain 108YD020 (FIG. 1) was observed at a concentration of $10^{-2}$ on the BN agar. The resultant white fungus colony was again streaked on malt extract agar to carry out pure isolation. The acclimated fungi were scraped by a platinum loop, placed in a 40% glycerol stock, and preserved in a deep freezer at −70° C.

The optimal growth temperature of the strain 108YD020 was 28° C., and on the 4th day of incubation, a morphological change showing white spores with a brownish center was observed. In liquid culture, the best growth was observed in artificial seawater with a salt concentration of 32 g/L. As a result of 18S rRNA gene sequencing to identify the strain and determine the phylogenetic location thereof, the strain was identified as *Penicillium* sp., which was then deposited as Accession Number KCTC 13190BP in the Korean Collection for Type Cultures on 26 Jan. 2017.

Figure 2:
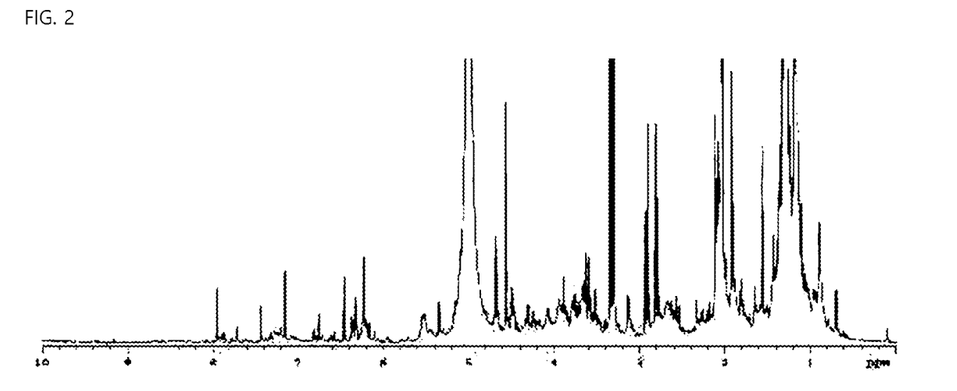
FIG. 2 is the $^1$H NMR spectrum of a culture extract of the strain 108YD020.

The strains stored in the 40% glycerol stock were taken out from the deep freezer at −70□, inoculated on malt extract agar medium in an aseptic environment, and then incubated in the B.O.D incubator at 28° C. The strains with an excellent growth rate were selected from the solid medium and inoculated into a 100-ml flask containing 50 ml of malt extract liquid medium, and then small scale incubation was carried out at 28° C. for 7 days in a shaking incubator at 120 rpm. The culture was subjected to extraction for 30 min twice with 50 ml of EtOAc, equal to the volume of the culture, and concentrated through a vacuum concentrator to thereby obtain an extract, which was then dissolved in MeOH-$d_4$ and observed by $^1$H NMR (see FIG. 2). To secure the amounts of various compounds, observed in the down-field region, and separate the compounds, large scale incubation was carried out.

Figure 3:
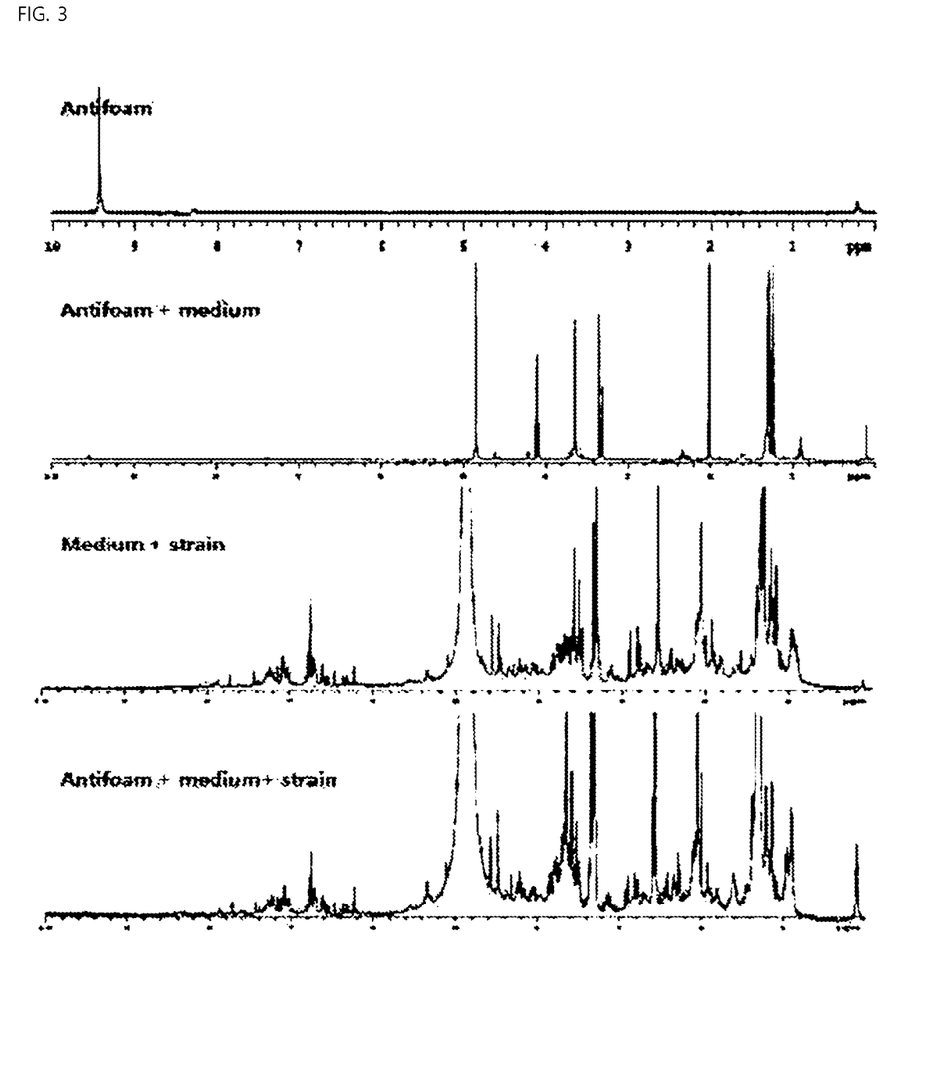
FIG. 3 is the $^1$H NMR spectra of a culture extract of the strain 108YD020 with respect to antifoam agent test results.

To prevent the overflow of a medium from a 100-L fermentor, an antifoam agent test was performed before the large scale incubation. As shown in FIG. 3, EA extraction followed by concentration was carried out under the four conditions to check NMR data. The antifoam agent was determined to have no effect on cell growth, and thus the antifoam agent was used in the large scale incubation. After 500 ml of the seed culture was inoculated into the 100-L fermentor with 50 L of malt extract medium containing a 0.1% antifoam agent, secondary large scale incubation was carried out at 28° C. for 7 days under the conditions of 32 g/L sea salt and 40 rpm. On the 4th day of incubation, 100 mL of the culture was taken out, subjected to extraction with EtOAc, and observed by $^1$H NMR to identify the growth and reproducibility of the cells, and then on the 7th day of incubation, the culture was harvested.

Next, the extraction, separation, and purification of compounds from cultures and the characterization of conformations of the compounds will be described.

The culture obtained from the incubation for 7 days was separated into a culture and cells by a centrifuge under the condition of 60,000 rpm. The culture was mixed with the same volume of 50 ml of EtOAc, and the mixture was subjected to extraction for 30 min twice by using a stirrer. The cells separated from the culture were subjected to extraction with MeOH at room temperature for 30 min. The culture and the cells were completely subjected to extraction and then concentrated by a vacuum concentrator, thereby obtaining an extract.

Figure 4:
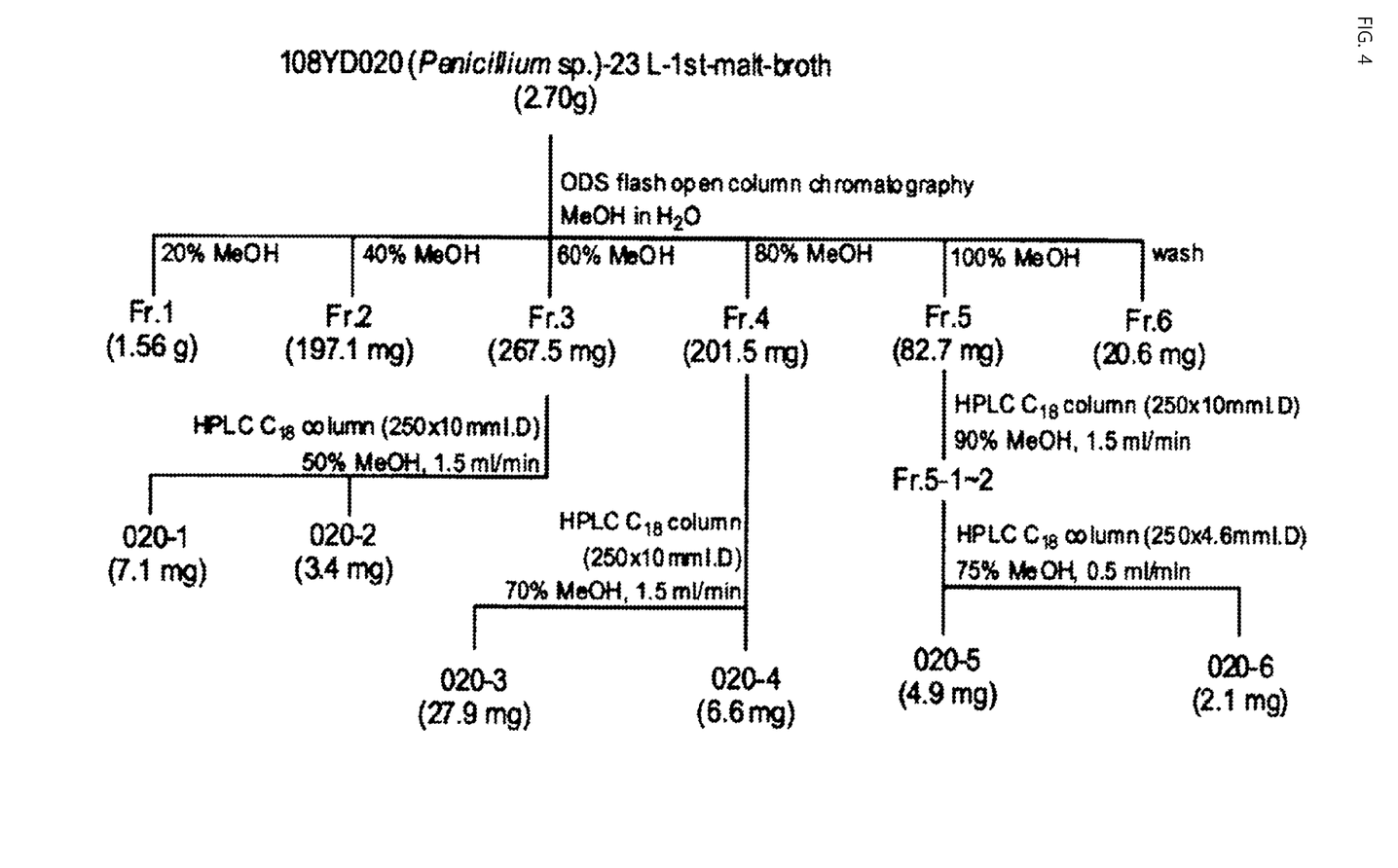
FIG. 4 schematically shows isolation and purification processes of a culture extract.

The extract of 2.70 g was dissolved in MeOH, and purified by RP-18 silica gel column chromatography. A mixture of MeOH and $H_2O$ was used as an extraction solvent, and the stepwise gradient was used in the order of MeOH:$H_2O$ 2:8 (Fraction 1), MeOH:$H_2O$ 4:6 (Fraction 2), MeOH:$H_2O$ 6:4 (Fraction 3), MeOH:$H_2O$ 8:2 (Fraction 4), MeOH (Fraction 5), and wash (Fraction 6). The respective fractions were concentrated under reduced pressure to secure Fraction 1 (1.56 g), Fraction 2 (197.1 mg), Fraction 3 (267.5 mg), Fraction 4 (201.5 mg), Fraction 5 (82.7 mg), and Fraction 6 (20.6 mg). A novel substance was purely separated from Fraction 3 by using RP-18 HPLC with the mobile phase 50% MeOH. A scheme for separation and purification of a substance from the culture extract is shown in FIG. 4.

The 60% MeOH fraction (287.5 mg) obtained by purifying the culture extract through $C_{18}$ reversed-phase vacuum flash chromatography was dissolved in MeOH, and then separated by reversed-phase HPLC (column: YMC-Pack ODS-A, particle diameter of 5 μm, 250×10 mm (length× inner diameter); and mobile phase: 50% MeOH, elution rate 1.5 ml/min, RI detector) to yield 7.1 mg of a compound represented by Formula 1 at $t_R$=69 min.

The compound represented by Formula 1 was a brown amorphous solid, and the molecular formula thereof was determined to be $C_{11}H_{14}O_3$ through HR-ESI-MS data m/z 193.0866 (calcd. m/z 193.0865 [M-H]$^-$), a degree of unsaturation of 5.5, and $^{13}C$ NMR data. In the IR spectrum, functional groups were confirmed by 1664 cm$^{-1}$ (C=C) and 2944 cm$^{-1}$ (sp$^3$ C—H). In addition, maximal absorbance values of log ε=4.66 and 4.15 were confirmed at UV 215 nm and 297 nm, respectively. Through the gHSQC experiment, four methyl groups and one olefin group were confirmed.

Figure 5:
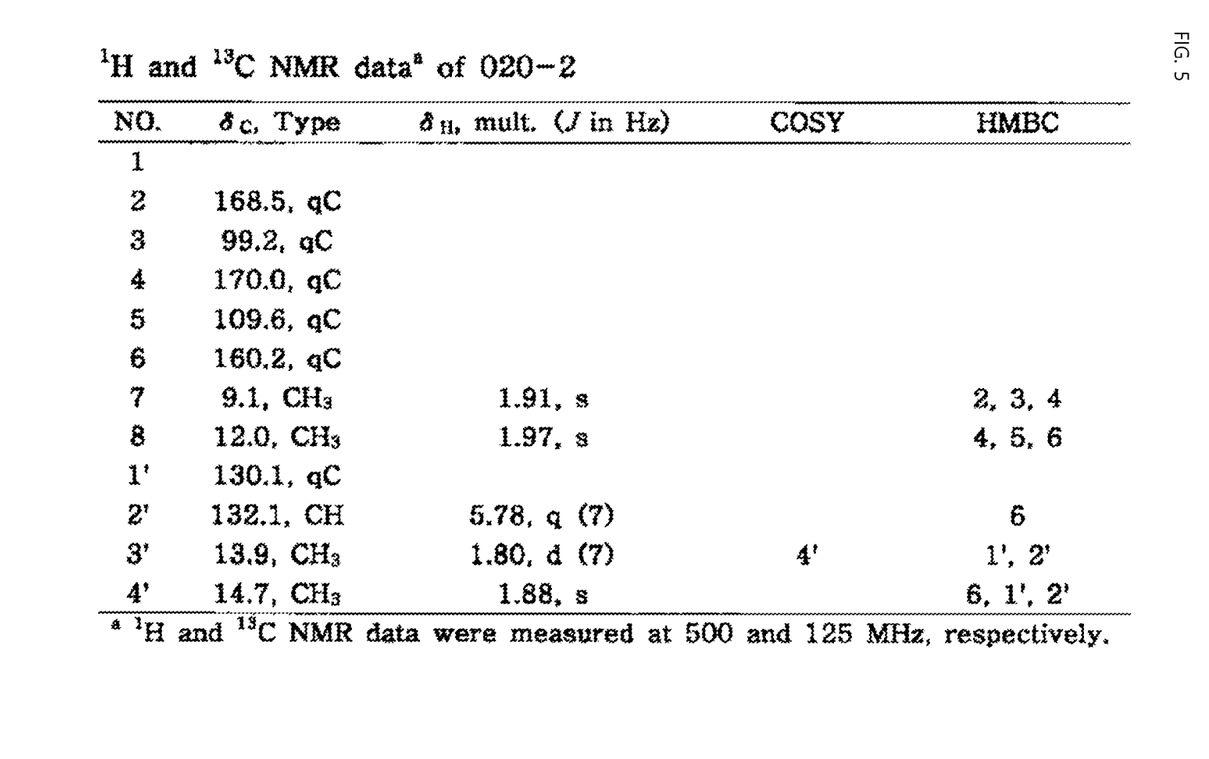
FIG. 5 shows $^1$H and $^{13}$C NMR data of a compound represented by Formula 1 according to the present disclosure.

The $^1H$ NMR data (see FIG. 5) indicates the presence of one olefinic proton H-2' ($\delta_H$ 5.78) and four methyl protons (H-7 ($\delta_H$ 1.91), H-8 ($\delta_H$ 1.97), H-3' ($\delta_H$ 1.80), and H-4' ($\delta_H$ 1.88)). The $^{13}C$ NMR data (FIG. 5) indicates the presence of five olefinic carbons (C-3 ($\delta_C$ 99.2), C-5 ($\delta_C$ 109.6), C-6 ($\delta_C$ 160.2), C-1' ($\delta_C$ 130.1), C-2' ($\delta_C$ 132.1)), four methyl carbons (C-7 ($\delta_C$ 9.1), C-8 ($\delta_C$ 12.0), C-3' ($\delta_C$ 13.9), C-4' ($\delta_C$ 14.7)), one oxygenated sp$^2$ quaternary carbon C-2 ($\delta_C$ 168.5), one carboxyl carbon C-4 ($\delta_C$ 170.0).

Figure 6:
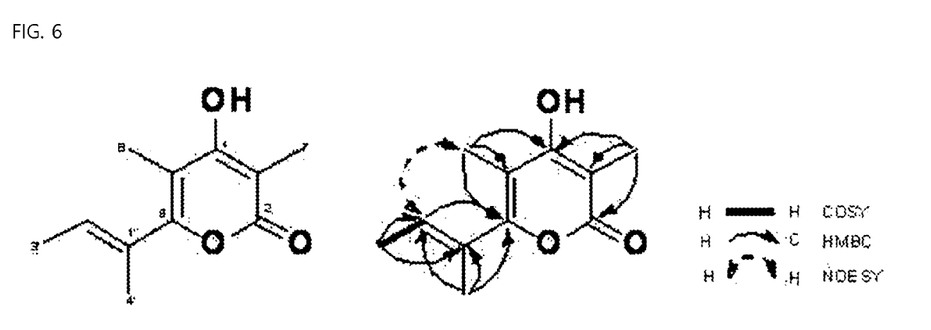
FIG. 6 schematically shows the conformation of a compound represented by Formula 1 according to the present disclosure and the COSY and HMBC correlations thereof.

It can be seen through gCOSY that H-2' ($\delta_H$ 5.78) and H-3' ($\delta_H$ 1.80) are spatially adjacent to each other, and it can be seen through the NOESY spectrum that protons were adjacent to each other in the three-dimensional structure by the correlations of H-8 ($\delta_H$ 1.97) and H-2' ($\delta_H$ 5.78) (see FIG. 6). It can be seen from gHMBC that the positions of carbon atoms constituting the pyran ring were identified by the correlations between H-7 ($\delta_H$ 1.91) and C-2 ($\delta_C$ 168.5), C-3 ($\delta_C$ 99.2), and C-4 ($\delta_C$ 170.0) and the correlation between H-8 ($\delta_H$ 1.97) and C-4 ($\delta_C$ 170.0), C-5 ($\delta_C$ 109.6), C-6 ($\delta_C$ 160.2), and C-6 ($\delta_C$ 160.2) and that side chains are linked to the pyran ring by the correlations between C-6 ($\delta_C$ 160.2) and H-2 ($\delta_H$ 5.78) and H-4' ($\delta_H$ 1.88), so that the conformation of a compound represented by Formula 1 was determined (see FIG. 6).

It can be seen that the compound represented by Formula 1 has a structure in which methyl groups are introduced at C-3 and C-5 and a hydroxyl group instead of a methoxyl group is introduced at C-4 in the structure of demethyl nectriapyrone A. As a result of literature search, the compound represented by Formula 1 was identified as a novel substance that has been isolated neither from nature so far, nor from *Penicillium* sp., and the structural formula thereof is as follows:

[Formula 1]

As a result of studying a compound, which is obtained by linking substituents to several positions of the compound represented by Formula 1 obtained by the above-described microorganism deposited as Accession Number KCTC 13190BP and has an equivalent effect to the compound represented by Formula 1, such a compound may be defined as a compound of Formula 2 below. Therefore, the purposes of the present disclosure are to provide, as a novel substance, a compound represented by Formula 2 including the compound represented by Formula 1, and to establish a use of the novel substance.

[Formula 2]

In the formula above:

$R_1$ is any one selected from the group consisting of H, OH, COOH, alkyl having 1 to 6 carbon atoms, and alkoxy having 1 to 6 carbon atoms;

$R_2$ is any one selected from the group consisting of H, OH, COOH, alkyl having 1 to 6 carbon atoms, and alkoxy having 1 to 6 carbon atoms;

$R_3$ is any one selected from the group consisting of H, OH, COOH, alkyl having 1 to 6 carbon atoms, and alkoxy having 1 to 6 carbon atoms; and $R_4$ is any one selected from the group consisting of H, OH, COOH, alkyl having 1 to 6 carbon atoms, and alkoxy having 1 to 6 carbon atoms.

Next, anti-wrinkle activity and skin whitening activity of the compound represented by Formula 1 or 2 will be described through test examples.

Test Example 1: Test on Increase in Collagen Synthesis with Respect to Anti-Wrinkle Activity Out of the compounds represented by Formula 2, the compounds according to the present disclosure shown in Table 1 were tested for collagen synthesis stimulating activity by addition to cultures of human-derived fibroblasts.

TABLE 1

|  | $R_1$ | $R_2$ | $R_3$ | $R_4$ |
|---|---|---|---|---|
| Compound 1 | H | OH | H | H |
| Compound 2 | $CH_3$ | OH | $CH_3$ | $CH_3$ |
| Compound 3 | $CH_2CH_3$ | OH | $CH_2CH_3$ | $CH_2CH_3$ |
| Compound 4 | H | OH | COOH | H |
| Compound 5 | $CH_3$ | H | $CH_3$ | $CH_3$ |
| Compound 6 | H | OH | H | $CH_2OH$ |
| Compound 7 | H | OH | H | $CHCH_3CHCH_3$ |
| Compound 8 | H | OH | H | $CHCH_3CHCH_2CH_3$ |
| Compound 9 | $CH_2CH_3$ | $CH_3$ | COOH | $CH_2OH$ |
| Compound 10 | $CH_2CH_3$ | $CH_3$ | $CH_2CH_3$ | $CH_2CH_3$ |

The measurement of synthesized collagen was conducted by quantification using a procollagen type I C-peptide enzyme immunoassay kit (PICP EIA kit).

Prior to testing, the toxicity of test substances at 10 ppm, 1 ppm, 0.1 ppm, 0.01 ppm, and 0.001 ppm on human-derived fibroblasts was assessed by MTT assay. For the MTT assay, the method used is disclosed in Mossman T. (1983), Rapid colorimetric assay for cellular growth & survival: application to proliferation & cytotoxicity assays, Journal of Immunological Methods vol. 65, pp. 55-63.

Collagen synthetic ability was evaluated by selecting the concentrations causing no toxicity on the basis of cytotoxicity results.

In the test, the final concentration of the compounds of the present disclosure was set to 20 ppm. Each sample was added to the culture medium of human fibroblasts, followed by incubation for one day, and then the culture was taken out, and the degree of collagen synthesis was measured at each concentration through the PICP EIA kit by using a spectrometer at 450 nm. For comparison of effects, the degree of collagen synthesis was measured by the same method on a culture medium of fibroblasts with nothing added (control) and a sample with vitamin C added to a final concentration of 20 ppm. The amount of collagen production was measured as a UV absorbance, and the rate of increase in collagen production was calculated as a ratio of collagen production relative to the collagen production of the control. The results are shown in Table 2 below.

TABLE 2

| Sample | Average absorbance | Collagen increase (%) |
|---|---|---|
| Control | 189 | |
| Compound 1 | 287.65 | 152.2 |
| Compound 2 | 287.24 | 147.2 |
| Compound 3 | 287.24 | 147.2 |
| Compound 4 | 287.61 | 152.1 |
| Compound 5 | 287.65 | 152.2 |
| Compound 6 | 287.61 | 152.1 |
| Compound 7 | 287.24 | 147.2 |
| Compound 8 | 287.65 | 152.2 |
| Compound 9 | 287.61 | 152.1 |
| Compound 10 | 287.24 | 147.2 |
| Vitamin C | 217.35 | 115.3 |

As shown in Table 2 above, the compounds according to the present disclosure would show a significantly excellent collagen increase rate relative to vitamin C, and thus it was determined that the compounds of the present disclosure would exhibit an excellent anti-wrinkle effect when used as a cosmetic raw material.

Test Example 2: Test on Melanogenesis Inhibition with Respect to Skin Whitening Activity The compounds shown in Table 1 were set to have final concentrations of 2 ppm and 20 ppm, and each of the compounds was added to a culture medium of B-16 melanoma cells, followed by incubation for 3 days. Thereafter, the cells were treated with trypsin, detached from the incubator, and centrifuged, and then melanin was extracted therefrom. The melanin was dissolved by addition of 1 mL of a sodium hydroxide solution (1 N) and boiling for 10 min, and then the absorbance was measured at 400 nm using a spectrometer, thereby determining the amount of melanin produced. The amount of melanin was measured as an absorbance per unit cell count ($10^6$ cells), and the amount of melanin production relative to the control with nothing added was calculated as an inhibition (%). The results were summarized in Table 3. The test was repeated three times.

To compare melanogenesis inhibiting activity of the compounds according to the present disclosure, 20 ppm arbutin was also tested by the same method, and the results are also shown in Table 3.

TABLE 3

| Sample | Amount of melanin produced | Inhibition (%) |
|---|---|---|
| Control (no addition) | 0.060 ± 0.002 | |
| Arbutin (final concentration: 20 ppm) | 0.056 ± 0.001 | 6.5% |
| Compound 1 (final concentration: 20 ppm) | 0.046 ± 0.001 | 23.5% |
| Compound 1 (final concentration: 2 ppm) | 0.047 ± 0.001 | 21.8% |
| Compound 2 (final concentration: 20 ppm) | 0.046 ± 0.001 | 23.5% |
| Compound 2 (final concentration: 2 ppm) | 0.048 ± 0.001 | 20.0% |
| Compound 3 (final concentration: 20 ppm) | 0.047 ± 0.001 | 21.8% |
| Compound 3 (final concentration: 2 ppm) | 0.048 ± 0.001 | 20.0% |
| Compound 4 (final concentration: 20 ppm) | 0.046 ± 0.001 | 23.5% |
| Compound 4 (final concentration: 2 ppm) | 0.048 ± 0.001 | 20.0% |
| Compound 5 (final concentration: 20 ppm) | 0.047 ± 0.001 | 21.8% |
| Compound 5 (final concentration: 2 ppm) | 0.049 ± 0.001 | 18.3% |
| Compound 6 (final concentration: 20 ppm) | 0.046 ± 0.001 | 23.5% |
| Compound 6 (final concentration: 2 ppm) | 0.048 ± 0.001 | 18.3% |
| Compound 7 (final concentration: 20 ppm) | 0.047 ± 0.001 | 21.8% |
| Compound 7 (final concentration: 2 ppm) | 0.049 ± 0.001 | 18.3% |
| Compound 8 (final concentration: 20 ppm) | 0.047 ± 0.001 | 21.8% |
| Compound 8 (final concentration: 2 ppm) | 0.049 ± 0.001 | 18.3% |
| Compound 9 (final concentration: 20 ppm) | 0.047 ± 0.001 | 21.8% |
| Compound 9 (final concentration: 2 ppm) | 0.049 ± 0.001 | 18.3% |
| Compound 10 (final concentration: 20 ppm) | 0.047 ± 0.001 | 21.8% |
| Compound 10 (final concentration: 2 ppm) | 0.049 ± 0.001 | 18.3% |

As shown in Table 3 above, the compounds according to the present disclosure was verified to show a significantly excellent melanogenesis inhibiting effect compared with arbutin, and thus it was determined that the compounds according to the present disclosure would show an excellent skin whitening effect when used as a raw material for a cosmetic product.

The above-described compounds represented by Formula 1 or 2 according to the present disclosure exhibit an excellent collagen synthesis stimulating effect and melanogenesis inhibiting effect, and thus can be used as an active ingredient in medicinal products, cosmetic materials, health foods, and the like for skin wrinkle relief, elasticity enhancement, and skin whitening.

Accordingly, the present disclosure provides a pharmaceutical composition for skin wrinkle relief, elasticity enhancement, and skin whitening, the pharmaceutical composition containing, as an active ingredient, a compound represented by Formula 1 or 2.

The pharmaceutical composition for skin wrinkle relief and elasticity enhancement of the present disclosure may contain a pharmaceutically acceptable salt of the compound represented by Formula 1.

The pharmaceutically acceptable salt of the compound represented by Formula 1 or 2 may be an acid addition salt formed using an organic acid or inorganic acid. Examples of the organic acid include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, dichloroacetic acid, aminooxy acetic acid, benzensulfonic acid, p-toluenesulfonic acid, and a methanesulfonic acid-based salt, and examples of the inorganic acid may include chloric acid, bromic acid, sulfuric acid, phosphoric acid, nitric acid, carbonic acid, and a boric acid-based salt. The acid addition salt may be preferably in the form of a chloric acid salt or acetic acid salt, and more preferably in the form of a chloric acid salt.

The above-mentioned acid addition salt may be prepared by a general salt preparation method, including: a) directly mixing the compound represented by Formula 1 or 2 with an acid; b) dissolving one of the compound and the acid in a solvent or a hydrated solvent, followed by mixing; or c) adding the compound represented by Formula 1 or 2 to an acid in a solvent or a hydrated solvent, followed by mixing.

Separately, additionally possible salt forms may be a GABA salt, a gabapentin salt, a pregabalin salt, a nicotine salt, an adipate salt, a hemi-malonic acid salt, a cysteine salt, an acetyl cysteine salt, a methionine salt, an arginine salt, a lysine slat, an ornithine salt, an aspartic acid salt, and the like.

The compound represented by Formula 1 or 2 or a pharmaceutically acceptable salt thereof, contained in the pharmaceutical composition of the present disclosure, may be contained in 0.0001-10 wt % relative to the entire pharmaceutical composition. More specifically, the compound or salt may be contained in 0.001-1 wt %. The composition of the present disclosure cannot be expected to have sufficient wrinkle reliving, elasticity enhancing, and skin whitening effects when containing less than 0.0001 wt % of the compound represented by Formula 1 or 2, and may be problematic with stability of a composition formulation when containing more than 10 wt % of the compound represented by Formula 1 or 2.

When the compound represented by Formula 1 or 2 is used as a medicinal product, such a medicinal product may further contain at least one active ingredient showing the same or similar functions compared to the compound represented by Formula 1 or 2. For example, a known skin wrinkle relieving substance or elasticity enhancing substance may be contained. The composition of the present disclosure, when containing an additional skin wrinkle relieving component, an elasticity enhancing component, and a skin whitening component, can have a further increased wrinkle reliving effect and elasticity enhancing effect. The above components may be added considering skin safety, easiness of formulation, and stability of active ingredients, according to the combined use. The composition may further contain, as a skin wrinkle relieving component known in the art, at least one skin wrinkle relieving component selected from the group consisting of retinoic acid, TGF, animal placenta-derived proteins, betulinic acid, and a chlorella extract.

In addition, the pharmaceutical composition for skin wrinkle relief and elasticity enhancement of the present disclosure may further contain a pharmaceutically acceptable carrier.

The pharmaceutically acceptable carrier may include a variety of components, such as a buffer, injectable sterile water, normal saline or phosphate buffered saline, sucrose, histidine, a salt, a polysorbate, and the like.

The pharmaceutical composition of the present disclosure may be administered orally or parenterally, and may be administered in the form of a general medicinal preparation, for example, various formulations for oral and parenteral administration upon clinical administration. The pharmaceutical composition may be formulated using a commonly used diluent or excipient, such as a filler, an extender, a binder, a wetting agent, a disintegrant, or a surfactant.

Examples of solid preparations for oral administration include a tablet, a pill, a powder, granules, a capsule, and the like. These solid preparations may be prepared by mixing the pharmaceutical composition of the present disclosure with at least one excipient, such as starch, calcium carbonate, sucrose or lactose, or gelatin.

In addition to simple excipients, lubricants, such as magnesium stearate and talc, may also be used. Examples of liquid preparations for oral administration may correspond to a suspension, a liquid for internal use, an emulsion, a syrup, and the like, and may include simple diluents that are frequently used, such as water and liquid paraffin, as well as various types of excipients, such as a wetting agent, a sweetener, an aroma, and a preservative.

Examples of preparations for parenteral administration include a sterile aqueous solution, a non-aqueous solvent, a suspension, an emulsion, a lyophilizer, and a suppository. As the non-aqueous solvent or suspension, propylene glycol, polyethylene glycol, a vegetable oil such as olive oil, injectable ester such as ethylolate, or the like may be used. As a base for the suppository, Witepsol, Macrogol, Twin 61, cacao butter, laurin butter, glycerogelatin, or the like may be used.

The present disclosure provides an externally-applied dermal preparation composition for skin wrinkle relief, elasticity enhancement, and skin whitening, the externally-applied dermal preparation composition containing a compound represented by Formula 1 or 2.

When the compound represented by Formula 1 or 2 is used as an externally-applied dermal preparation composition, such an externally-applied dermal preparation composition may further contain an adjuvant that is commonly used in the field of dermatology, for example, a fatty substance, an organic solvent, a solubilizing agent, a thickening agent, a gelling agent, a softening agent, an antioxidant, a suspending agent, a stabilizer, a forming agent, an aroma, a surfactant, water, an ionic or nonionic emulsifier, a filler, a sequestering agent, a chelating agent, a preservative, a vitamin, a blocking agent, a wetting agent, an essential oil, a dye, a pigment, a hydrophilic or lipophilic activator, lipid vesicles, or any other component used in an external preparation for skin. The above components may be introduced in amounts that are commonly used in dermatology.

When the compound represented by Formula 1 or 2 is used in the formulation of an externally-applied dermal preparation, such an externally-applied dermal preparation may have a formulation, such as an ointment, a patch, a gel, a cream, or a sprayer, but is not limited thereto.

The compound represented by Formula 1 or 2 contained in the externally-applied dermal preparation composition for skin wrinkle relief, elasticity enhancement, and skin whitening of the present disclosure may be contained in a content of 0.0001-10 wt % relative to the total weight of the externally-applied dermal preparation composition. Less than 0.0001 wt % of the compound cannot be expected to have sufficient wrinkle reliving, elasticity enhancing, and skin whitening effects, and more than 10 wt % of the compound may cause problems in chemical stability of the composition.

The present disclosure provides a cosmetic composition for skin wrinkle relief, elasticity enhancement, and skin whitening, the cosmetic composition containing a compound represented by Formula 1 or 2.

When the compound represented by Formula 1 or 2 is used for a cosmetic product, a cosmetic product containing the compound represented by Formula 1 as an active ingredient may be prepared as a general emulsified formulation and solubilized formulation. For example, the cosmetic product may be in the formulation of: an emollient, such as a soft emollient or a nutritional emollient; a lotion, such as a facial lotion or a body lotion; a cream, such as a nutrition cream, a moisture cream or an eye cream; essence; a cosmetic ointment; a spray; a gel; a pack; a sunscreen; a make-up base; a foundation, such as a liquid-type foundation, a solid-type foundation, or spray-type foundation; a powder; a make-up remover, such as a cleansing cream, a cleansing lotion, or a cleansing oil; and a cleaner, such as a cleansing foam, a soap, or a body washer.

The cosmetic composition may further contain an adjurvant and a carrier that are commonly used in a cosmetic composition, such as a stabilizer, a solubilizer, a vitamin, a dye, or an aroma, in addition to the compound represented by Formula 1 or 2. The cosmetic composition may contain an adjurvant that is commonly used in the cosmetology, for example, a fatty substance, an organic solvent, a solubilizing agent, a thickening agent, a gelling agent, a softening agent, an antioxidant, a suspending agent, a stabilizer, a foaming agent, an aroma, a surfactant, water, an ionic or nonionic emulsifier, a filler, a sequestering agent, a chelating agent, a preservative, a vitamin, a blocking agent, a wetting agent, an essential oil, a dye, a pigment, a hydrophilic or lipophilic activator, lipid vesicles, or any other component used in a cosmetic product.

The compound represented by Formula 1 or 2, when manufactured into a cosmetic product, may be contained at a relatively high concentration in a wash-off type cosmetic product, such as a make-up remover or a cleanser, of which an active ingredient stays on the skin for a short time. Whereas, the compound represented by Formula 1 or 2 may be contained at a lower concentration in a leave-on type cosmetic product, such as an emollient, a lotion, a cream, or an essence, of which an active ingredient stays on the skin for a long time, rather than in a wash-off type cosmetic product. In an embodiment of the present disclosure, the composition may contain the compound represented by Formula 1 in a content of 0.0001-10 wt % relative to the total weight of the composition, but is not limited thereto.

The present disclosure also relates to a health food for skin wrinkle relief, elasticity enhancement, and skin whitening, the health food containing a compound represented by Formula 1 or 2.

As used herein, the term "health food" refers to a food that is manufactured by adding the compound represented by Formula 1 or 2 to a food material, such as a drink, a tea, a spice, a gum, or cookies, or by means of encapsulation, powdering, or suspension, and has a particular healthful effect upon intake. Unlike general medicines, the health food employs a food as a raw material, and thus does not cause a side effect that may be caused due to the long-term use of a medicine.

Since the health food of the present disclosure thus obtained can be usually consumed, high skin wrinkle relieving, elasticity enhancing, and skin whitening effects of the health food can be expected, so that the health food of the present disclosure is very useful.

When the compound represented by Formula 1 or 2 is used as a food additive, the compound represented by Formula 1 or 2 can be added as it is, or used with another food or another food ingredient, and can be used as appropriate by a conventional method. The amount of the active ingredient mixed may be appropriately determined according to the purpose of use (prevention, health, or therapeutic treatment) thereof. The composition of the present disclosure is usually added in a content of 0.0001-10 wt % relative to raw materials when manufactured into a food or a drink. More specifically, the compound of the present disclosure may be added in a content of 0.001-1 wt %.

The kind of the food is not particularly limited. Examples of the food to which the above materials can be added include meat, sausage, bread, chocolate, candies, snacks, cookies, pizza, ramen, other noodles, gums, dairy products including ice cream, various soups, drinks, teas, drinks, alcoholic drinks, vitamin complexes, and the like, and encompass all foods in an acceptable meaning.

Similar to common drinks, the health drink of the present disclosure may contain various flavors or natural carbohydrates as additional ingredients. Examples of the above-described carbohydrates may include: monosaccharides, such as glucose and fructose; disaccharides such as maltose and sucrose; polysaccharides such as dextrin and cyclodextrin; and sugar alcohols, such as xylitol, sorbitol, and erythritol. Examples of the sweetener may include natural sweeteners, such as thaumatin and a stevia extract, and synthetic sweeteners, such as saccharin and aspartame.

In addition to above ingredients, the health food of the present disclosure may contain various nutritional agents, vitamins, electrolytes, flavors, colorants, pectic acid and salts thereof, alginic acid and salts thereof, organic acids, protective colloid thickeners, pH adjusters, stabilizers, stabilizing agents, preservatives, glycerins, alcohols, carbonating agents used in carbonated drinks, and the like.

Furthermore, the health food of the present disclosure may contain fruit flesh for manufacturing a natural fruit juice, a fruit juice drink, and a vegetable drink. These ingredients may be used independently or in mixture.

The invention claimed is:

1. A compound represented by Formula 1 below:

[Formula 1]

2. The compound of claim 1, wherein the compound represented by Formula 1 is prepared by a microorganism deposited as Accession Number KCTC 13190BP.

3. A pharmaceutical composition for skin wrinkle relief, elasticity enhancement, and skin whitening, the pharmaceutical composition comprising a compound represented by Formula 1 below:

[Formula 1]

4. The pharmaceutical composition of claim 3, wherein the compound is contained in 0.0001-10 wt % relative to the entire composition.

5. An externally-applied dermal preparation composition for skin wrinkle relief, elasticity enhancement, and skin whitening, the externally-applied dermal preparation composition comprising a compound represented by Formula 1 below:

[Formula 1]

6. The externally-applied dermal preparation composition of claim 5, wherein the compound is contained in 0.0001-10 wt % relative to the entire composition.

7. The externally-applied dermal preparation composition of claim 5, wherein the compound is contained in 0.0001-10 wt % relative to the entire composition.

8. A cosmetic composition for skin wrinkle relief, elasticity enhancement, and skin whitening, the cosmetic composition comprising a compound represented by Formula 1 below:

9. The cosmetic composition of claim 8, wherein the compound is contained in 0.0001-10 wt % relative to the entire composition.

10. The cosmetic composition of claim 8, wherein the compound is contained in 0.0001-10 wt % relative to the entire composition.

11. A health food composition for skin wrinkle relief, elasticity enhancement, and skin whitening, the health food composition comprising a compound represented by Formula 1 below:

[Formula 1]

12. The health food composition of claim 11, wherein the compound is contained in 0.0001-10 wt % relative to the entire composition.

13. The health food composition of claim 11, wherein the compound is contained in 0.0001-10 wt % relative to the entire composition.

* * * * *